(12) United States Patent
Bae et al.

(10) Patent No.: US 8,545,411 B2
(45) Date of Patent: Oct. 1, 2013

(54) ULTRASOUND SYSTEM AND METHOD FOR ADAPTIVELY PERFORMING CLUTTER FILTERING

(75) Inventors: Moo Ho Bae, Seoul (KR); Tae Yun Kim, Seoul (KR)

(73) Assignee: Medison Co., Ltd., Kangwon-Do (KR)

( * ) Notice: Subject to any disclaimer, the term of this patent is extended or adjusted under 35 U.S.C. 154(b) by 510 days.

(21) Appl. No.: 12/772,088

(22) Filed: Apr. 30, 2010

(65) Prior Publication Data

US 2010/0280386 A1   Nov. 4, 2010

(30) Foreign Application Priority Data

Apr. 30, 2009   (KR) .................. 10-2009-0038060
Apr. 14, 2010   (KR) .................. 10-2010-0034064

(51) Int. Cl.
*A61B 6/00*   (2006.01)

(52) U.S. Cl.
USPC .......................................... 600/454; 600/437

(58) Field of Classification Search
USPC ........................................................ 600/454
See application file for complete search history.

(56) References Cited

U.S. PATENT DOCUMENTS 4,932,415 A * 6/1990 Angelsen et al. ............ 600/455
5,226,420 A   7/1993 Peterson 2007/0167791 A1* 7/2007 Umemura et al. ............ 600/455
2009/0158858 A1* 6/2009 Gysling et al. ............ 73/861.27
2010/0130873 A1* 5/2010 Yuen et al. .................... 600/484

FOREIGN PATENT DOCUMENTS

| EP | 0 481 691 A1 | 4/1992 |
| EP | 1 548 462 A1 | 6/2005 |
| JP | 2004-195228 | 7/2004 |
| JP | 2008-149153 | 7/2008 |
| KR | 10-0352638 | 8/2002 |

OTHER PUBLICATIONS

Korean Office Action issued in Korean Patent Application No. 10-2010-0034064 dated Mar. 2, 2012.

(Continued)

*Primary Examiner* — Tse Chen
*Assistant Examiner* — Patricia Park
(74) *Attorney, Agent, or Firm* — McDermott Will & Emery LLP

(57) ABSTRACT

Embodiments of adaptively performing clutter filtering are disclosed. In one embodiment, by way of non-limiting example, an ultrasound system comprises: an ultrasound data acquisition unit configured to transmit and receive ultrasound signals to and from a target object to thereby output a plurality of ultrasound data for obtaining a color Doppler mode image, wherein the target object includes at least one of a tissue and a blood flow; and a processing unit placed in communication with the ultrasound data acquisition unit and being configured to locate the plurality of ultrasound data on a complex plane, the processing unit being further configured to perform a circle fitting upon the plurality of ultrasound data located on the complex plane and perform a downmixing and a clutter filtering upon the circle-fitted ultrasound data in consideration of speed of the tissue.

16 Claims, 15 Drawing Sheets

(56) References Cited

OTHER PUBLICATIONS

Extended European Search Report issued in European Patent Application No. EP 10160837.0 dated Apr. 29, 2013.

Byung-Kwon Park et al., "Arctangent Demodulation With DC Offset Compensation in Quadrature Doppler Radar Receiver Systems," IEEE Transactions on Microwave Theory and Techniques, vol. 55, No. 5, May 2007.

Xiaotao Wang et al., "An Novel Clutter Rejection Filters Applied to Wideband Blood Flow Velocity Estimation," Proceedings of the 2005 IEEE Engineering in Medicine and Biology 27 Annual Conference, Sep. 1-4, 2005.

Hans Torp, "Clutter Rejection Filters in Color Flow Imaging: A Theoretical Approach," IEEE Transactions on Ultrasonics, Ferroelectrics, and Frequency Control, vol. 44, No. 2, Mar. 1997.

* cited by examiner

ULTRASOUND SYSTEM AND METHOD FOR ADAPTIVELY PERFORMING CLUTTER FILTERING

CROSS-REFERENCE TO RELATED APPLICATIONS

The present application claims priority from Korean Patent Application Nos. 10-2009-0038060 (filed on Apr. 30, 2009) and 10-2010-0034064 (filed on Apr. 14, 2010), the entire subject matters of which are incorporated herein by reference.

TECHNICAL FIELD

The present disclosure generally relates to ultrasound systems, and more particularly to an ultrasound system and method for adaptively performing clutter filtering.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two or three-dimensional diagnostic images of internal features of an object (e.g., human organs).

As is known in the art, the ultrasound system may provide ultrasound images of various modes including a brightness mode (B mode) image representing reflection coefficients of the ultrasound signals reflected from the target object with a 2D (two-dimensional) image, a Doppler mode (D mode) image representing speed of a moving object with spectral Doppler by using a Doppler effect, a color Doppler mode (C mode) image representing speed of a moving object with colors by using the Doppler effect, and an elastic mode (E mode) image representing mechanical characteristics of tissues before and after applying a pressure thereto. In particular, the ultrasound system may transmit and receive ultrasound signals to and from the target object to thereby form Doppler signals. The ultrasound system may further form the C mode image representing the speed of the moving object with the colors based on the Doppler signals.

The Doppler signal may include a low frequency signal (so-called clutter signal) due to the motion of a tissue such as a blood vessel wall, a cardiac wall, a heart valve and the like. The clutter signal may have amplitude, which is over 100 times than that of a pure Doppler signal indicative of velocities of the blood flow. The clutter signal may be an obstacle to accurately detect speed of the blood flow. Thus, it is required to remove the clutter signal from the Doppler signal in order to accurately detect the speed of the blood flow.

A clutter downmixing has been used to remove the clutter signals. The downmixing may be carried out by estimating a center frequency of the clutter signals and by performing the downmixing (frequency shift), which shifts the center frequency of the clutter signals to 0, upon the Doppler signals based on the center frequency. Thereafter, the downmixed clutter signals, which are shifted to a DC component, may be removed by using the conventional clutter filtering methods.

The clutter signals may have a speed component when a tissue exists within the target object, wherein the tissue moves at a constant speed. However, the clutter signals may have two speed components when tissues exist within the target object, wherein the tissues comprise a tissue that does not move within the target object and a tissue that moves at the constant speed. Thus, it may be difficult to accurately perform the downmixing, which shifts the center of the clutter signals to 0, by using the conventional clutter downmixing methods. Further, the clutter signals may have a plurality of speed components when a tissue exists within the target object, wherein the tissue moves at a lower speed than a predetermined speed (e.g., minimum speed of blood flow). As such, it may be difficult to accurately perform the downmixing, which shifts the center of the clutter signals to 0, by using the conventional clutter downmixing methods.

SUMMARY

According to the present disclosure, there is disclosed an ultrasound system and method for adaptively performing a clutter filtering upon a plurality of ultrasound data in consideration of the speed of tissues (e.g., blood vessel wall) existing within a target object.

In one embodiment, by way of non-limiting example, an ultrasound system comprises: an ultrasound data acquisition unit configured to transmit and receive ultrasound signals to and from a target object to thereby output a plurality of ultrasound data for obtaining a color Doppler mode image, wherein the target object includes at least one of a tissue and a blood flow; and a processing unit placed in communication with the ultrasound data acquisition unit and being configured to locate the plurality of ultrasound data on a complex plane, the processing unit being further configured to perform a circle fitting upon the plurality of ultrasound data located on the complex plane and perform a downmixing and a clutter filtering upon the circle-fitted ultrasound data in consideration of speed of the tissue.

In another embodiment, there is provided a method of performing a clutter filtering, comprising: a) acquiring a plurality of ultrasound data corresponding to a target object including at least one of a tissue and a blood flow, wherein the plurality of ultrasound data are ultrasound data for obtaining a color Doppler mode image; b) locating each of the plurality of ultrasound data on a complex plane; c) performing a circle fitting on the plurality of ultrasound data located on the complex plane; and d) performing a downmixing and a clutter filtering on the circle-fitted ultrasound data in consideration of speed of the tissue.

In yet another embodiment, there is provided a computer readable medium comprising computer executable instructions configured to perform the following acts: a) acquiring a plurality of ultrasound data corresponding to a target object including at least one of a tissue and a blood flow, wherein the plurality of ultrasound data are ultrasound data for obtaining a color Doppler mode image; b) locating each of the plurality of ultrasound data on a complex plane; c) performing a circle fitting on the plurality of ultrasound data located on the complex plane; and d) performing a downmixing and a clutter filtering on the circle-fitted ultrasound data in consideration of speed of the tissue.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure. As used herein, the term "Doppler mode" comprises a color Doppler mode.

Figure 1:
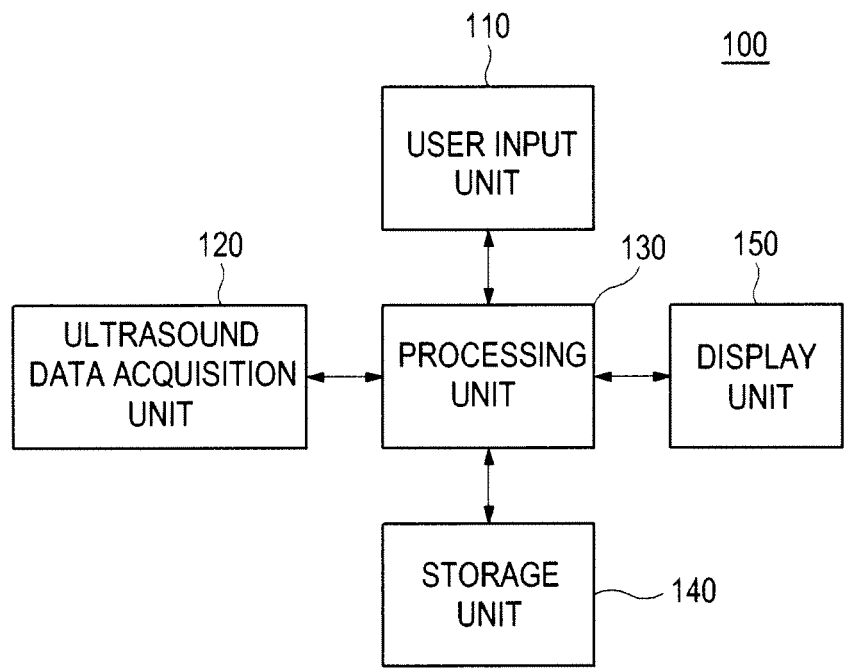
FIG. 1 is a block diagram showing an illustrative embodiment of an ultrasound system.

FIG. 1 is a block diagram showing an illustrative embodiment of an ultrasound system which embodies the methods of the present invention. Referring to FIG. 1, the ultrasound system 100 may include a user input unit 110, an ultrasound data acquisition unit 120, a processing unit 130, a storage unit 140 and a display unit 150.

Figure 2:
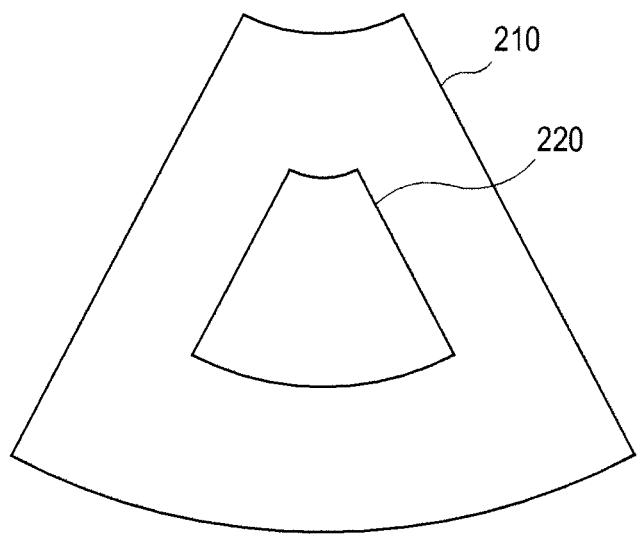
FIG. 2 is a schematic diagram showing an example of a brightness mode image and a region of interest (ROI).

The user input unit 110 may be configured to receive input information from a user. In one embodiment, the input information may include position and size information of a region of interest (ROI) 220, which may be set on a brightness mode image 210, as shown in FIG. 2. The ROI 220 may include a color box. Also, at least one of a plurality of scan-lines may be comprised within the ROI 220. The user input unit 110 may include a control panel, a keyboard, a mouse and the like.

The ultrasound data acquisition unit 120 may be configured to transmit and receive ultrasound signals to and from a target object to thereby acquire ultrasound data corresponding to the ROI (i.e., color box). The ultrasound data acquisition unit 120 will be described with reference to FIG. 3.

Figure 3:
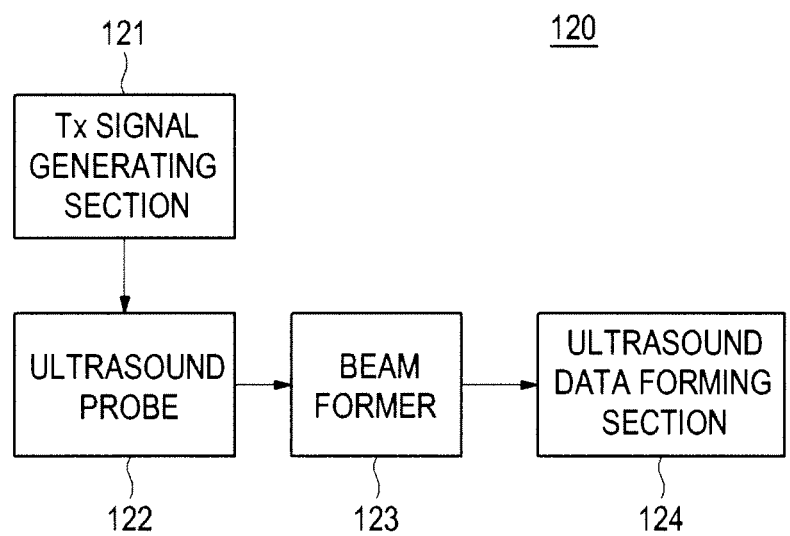
FIG. 3 is a block diagram showing an illustrative embodiment of an ultrasound data acquisition unit.

FIG. 3 is a block diagram showing an illustrative embodiment of the ultrasound data acquisition unit. Referring to FIG. 3, the ultrasound data acquisition unit 120 may include a transmit (Tx) signal generating section 121, an ultrasound probe 122 comprising a plurality of transducer elements (not shown), a beam former 123 and an ultrasound data forming section 124.

The Tx signal generating section 121 may be configured to generate Tx signals in consideration of focal points and positions of the transducer elements. The Tx signals may be signals for acquiring a Doppler mode image. The Tx signal generating section 121 may generate a plurality of Tx signals based on a predetermined ensemble number. The ensemble number may represent the number of transmitting and receiving ultrasound signals needed to acquire Doppler signals corresponding to a scan-line.

The ultrasound probe 122 may be configured to convert the Tx signals provided from the Tx signal generating section 121 into the ultrasound signals. The ultrasound probe 122 may further transmit the ultrasound signals into the target object, and receive ultrasound echo signals reflected from the target object to thereby form received signals, which may be analog signals. The ultrasound probe 122 may include a linear array probe, a convex array probe and the like.

The beam former 123 may be configured to convert the received signals provided from the ultrasound probe 122 into digital signals. The beam former 123 may further receive-focus the digital signals in consideration of the focal points and the positions of the transducer elements to thereby form receive-focused signals.

The ultrasound data forming section 124 may be configured to form the ultrasound data based on the receive-focused signals provided from the beam former 123. In one embodiment, the ultrasound data may include IQ (in-phase/quadrature) data (i.e., ensemble data) for acquiring the Doppler signals. The ultrasound data forming section 124 may form a plurality of ultrasound data corresponding to the ensemble number based on the receive-focused signals sequentially provided from the beam former 123.

Referring back to FIG. 1, the processing unit 130 may be coupled to the user input unit 110 and the ultrasound data acquisition unit 120. The processing unit 130 may be configured to adaptively perform clutter filtering upon the ultrasound data provided from the ultrasound data acquisition unit 120. The processing unit 130 may further form the Doppler mode image based on the clutter-filtered ultrasound data. The processing unit 130 will be described in detail with reference to FIG. 4.

Figure 4:
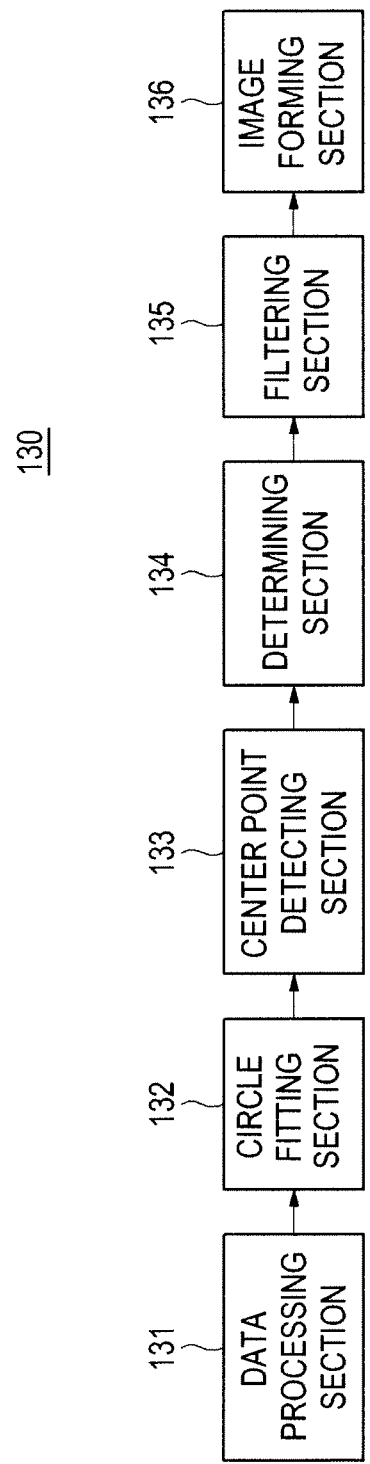
FIG. 4 is a block diagram showing an illustrative embodiment of a processing unit.

FIG. 4 is a block diagram showing an illustrative embodiment of the processing unit. Referring to FIG. 4, the processing unit 130 may include a data processing section 131, a circle fitting section 132, a center point detecting section 133, a determining section 134, a filtering section 135 and an image forming section 136.

The data processing section 131 may be configured to analyze the plurality of ultrasound data (i.e., ensemble data) provided from the ultrasound data acquisition unit 120 to thereby locate each of the plurality of ultrasound data on a complex plane.

Generally, the ultrasound data (i.e., ensemble data) corresponding to the ROI may be located on the complex plane in various shapes according to speeds of tissue (e.g., vessel wall), blood flow and the like, which exist within the target object.

Figure 5:
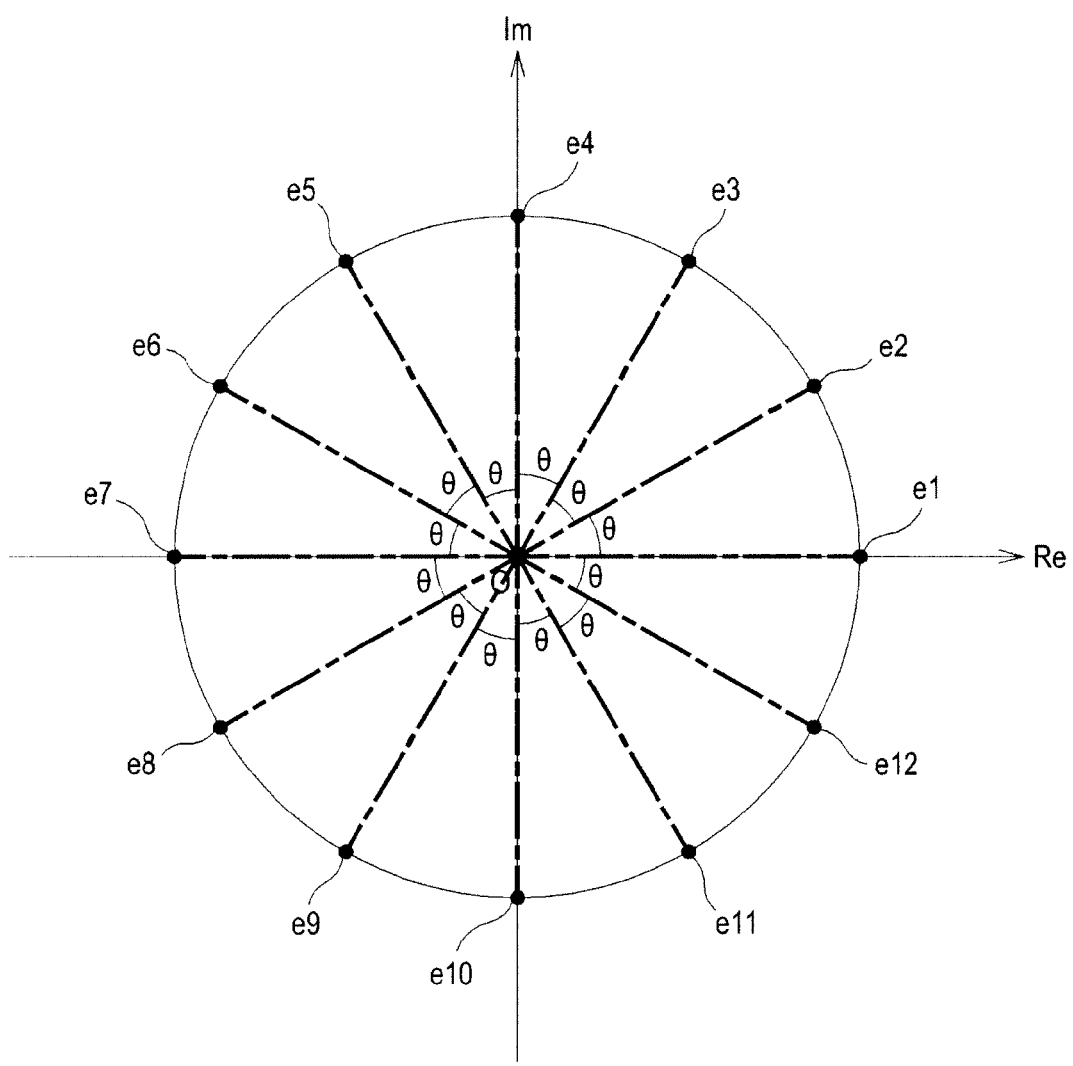
FIG. 5 is a schematic diagram showing an example of locating the plurality of ultrasound data corresponding to a tissue on the complex plane, wherein the tissue moves at constant speed within the target object.

FIG. 5 is a schematic diagram showing an example of locating the plurality of ultrasound data corresponding to a tissue on the complex plane, wherein the tissue moves at a constant speed within the target objet. Referring to FIG. 5, when the tissue moves at the constant speed within the target object, a plurality of ultrasound data e1 to e12 acquired from the tissue may be located on a circumference with a center point at an origin O of the complex plane. In addition, the plurality of ultrasound data e1 to e12 may be located on the circumference at constant interval θ.

Figure 6:
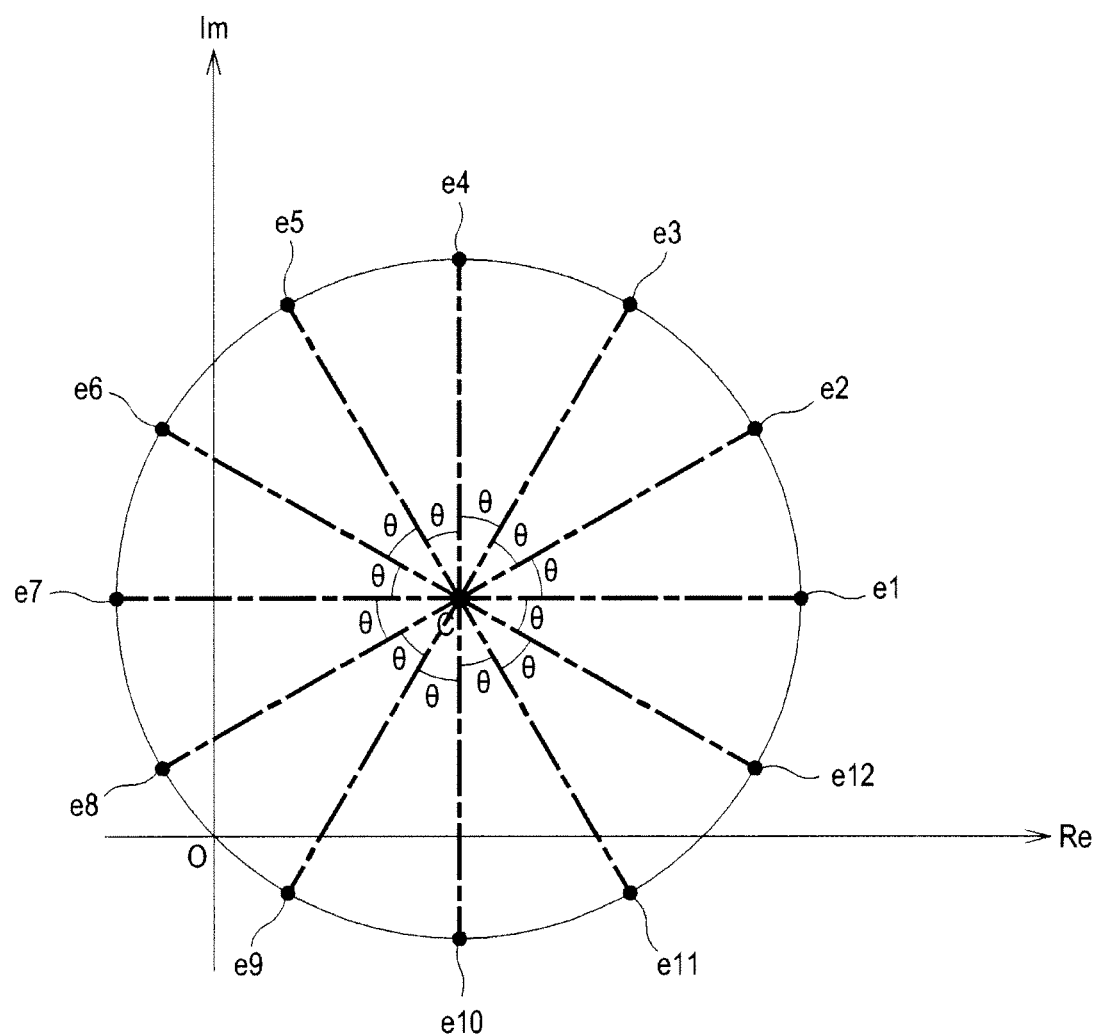
FIG. 6 is a schematic diagram showing an example of locating the plurality of ultrasound data corresponding to tissues on the complex plane, wherein the tissues comprise a tissue that does not move within the target object and a tissue that moves at constant speed within the target object.

FIG. 6 is a schematic diagram showing an example of locating the plurality of ultrasound data corresponding to tissues on the complex plane, wherein the tissues comprise a tissue that does not move within the target object and another tissue that moves at constant speed within the target object. Referring to FIG. 6, when the tissues comprise the tissue that does not move within the target object and the tissue that moves at the constant speed within the target object, a plurality of ultrasound data e1 to e12 acquired from the tissues may be located on a circumference with a speed component (i.e., DC component) of the tissue that does not move within the target object as a center point C apart from the origin O of the complex plane. In addition, the plurality of ultrasound data e1 to e12 may be located on the circumference at the constant interval θ.

Figure 7:
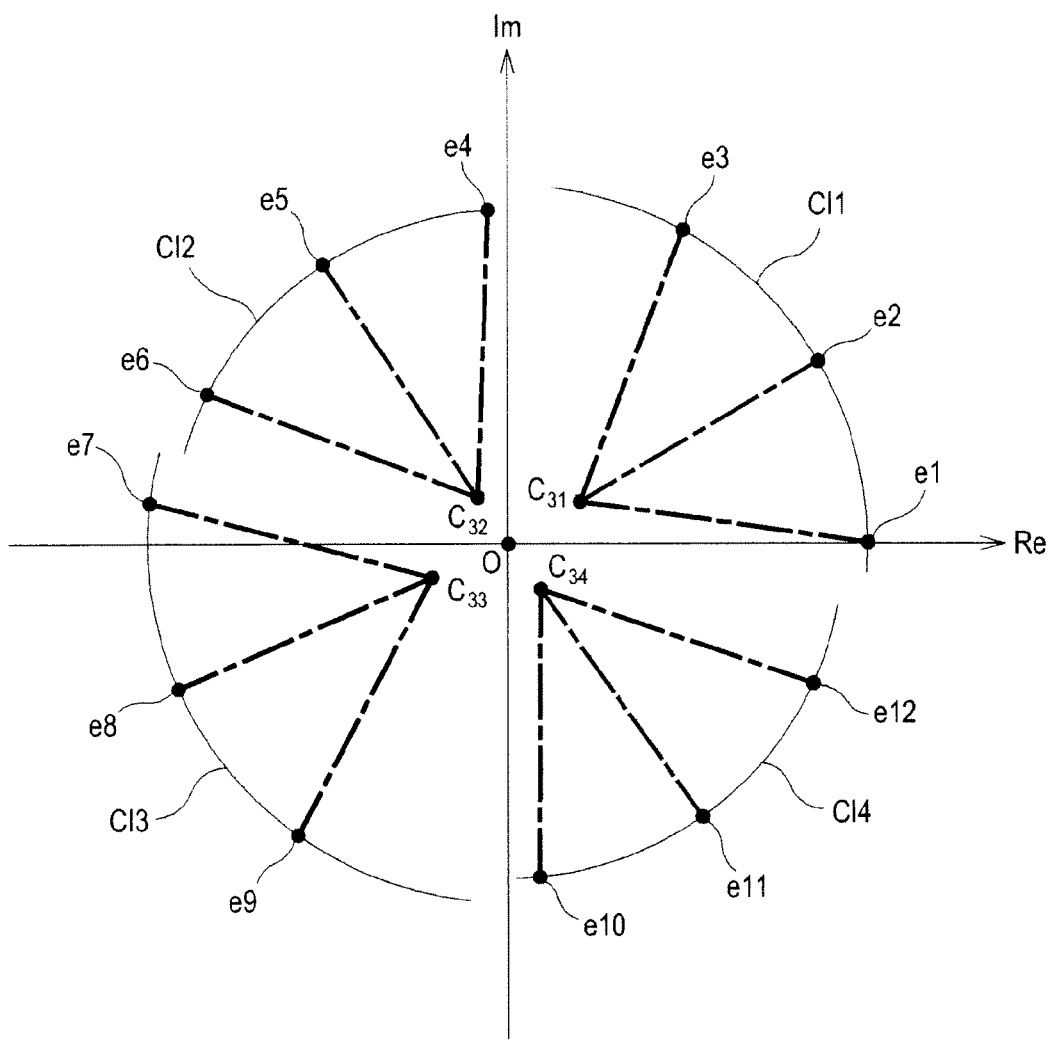
FIG. 7 is a schematic diagram showing an example of locating a plurality of ultrasound data corresponding to a tissue on the complex plane, wherein the tissue moves at a lower speed than a predetermined speed within the target object.

FIG. 7 is a schematic diagram showing an example of locating a plurality of ultrasound data corresponding to a tissue on the complex plane, wherein the tissue moves at a lower speed (hereinafter, "a low speed") than a predetermined speed within the target object. Referring to FIG. 7, when the tissue moves at the low speed within the target object, the ultrasound data e1 to e3 acquired from the tissue may be located on a circumference CI1, the ultrasound data e4 to e6 acquired from the tissue may be located on a circumference CI2, the ultrasound data e7 to e9 acquired from the tissue may be located on a circumference CI3, and the ultrasound data e10 to e12 acquired from the tissue may be located on a circumference CI4. Center points C31 to C34 of the circumferences CI1 to CI4 may not be located on the origin O of the complex plane, and may move slowly.

Examples of locating the plurality of ultrasound data, which correspond to the tissue and the blood flow that exist within the target object, on the complex plane in consideration of speeds of the tissue and the blood flow will be described in view of FIGS. 8 to 10.

Figure 8:
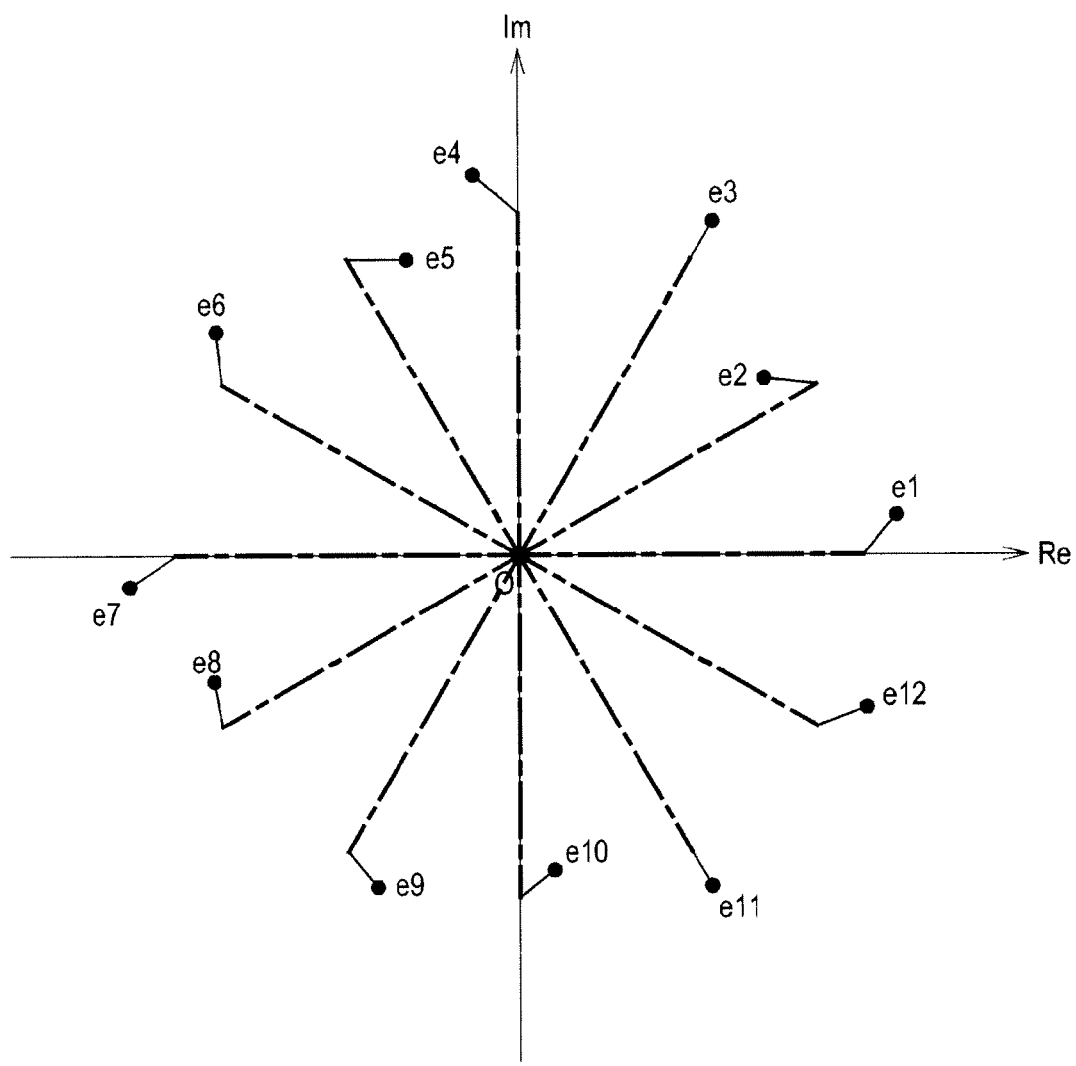
FIG. 8 is a schematic diagram showing an example of locating the plurality of ultrasound data corresponding to the tissue and the blood flow on the complex plane, wherein the tissue moves at the constant speed within the target object.

FIG. 8 is a schematic diagram showing an example of locating the plurality of ultrasound data, which correspond to the tissue and the blood flow, on the complex plane, wherein the tissue moves at the constant speed within the target object. The data processing section 131 may be configured to analyze the plurality of ultrasound data e1 to e12 acquired from the tissue and the blood flow. The data processing section 131 may further locate the plurality of ultrasound data e1 to e12, which overlap speed components (shown by dotted lines) corresponding to the tissue with speed components (shown by lines) corresponding to the blood flow, on the complex plane as shown in FIG. 8. The plurality of ultrasound data e1 to e12 may be located on the complex plane with the center point at the origin O of the complex plane. In one embodiment, the overlap may represent sum of phases.

Figure 9:
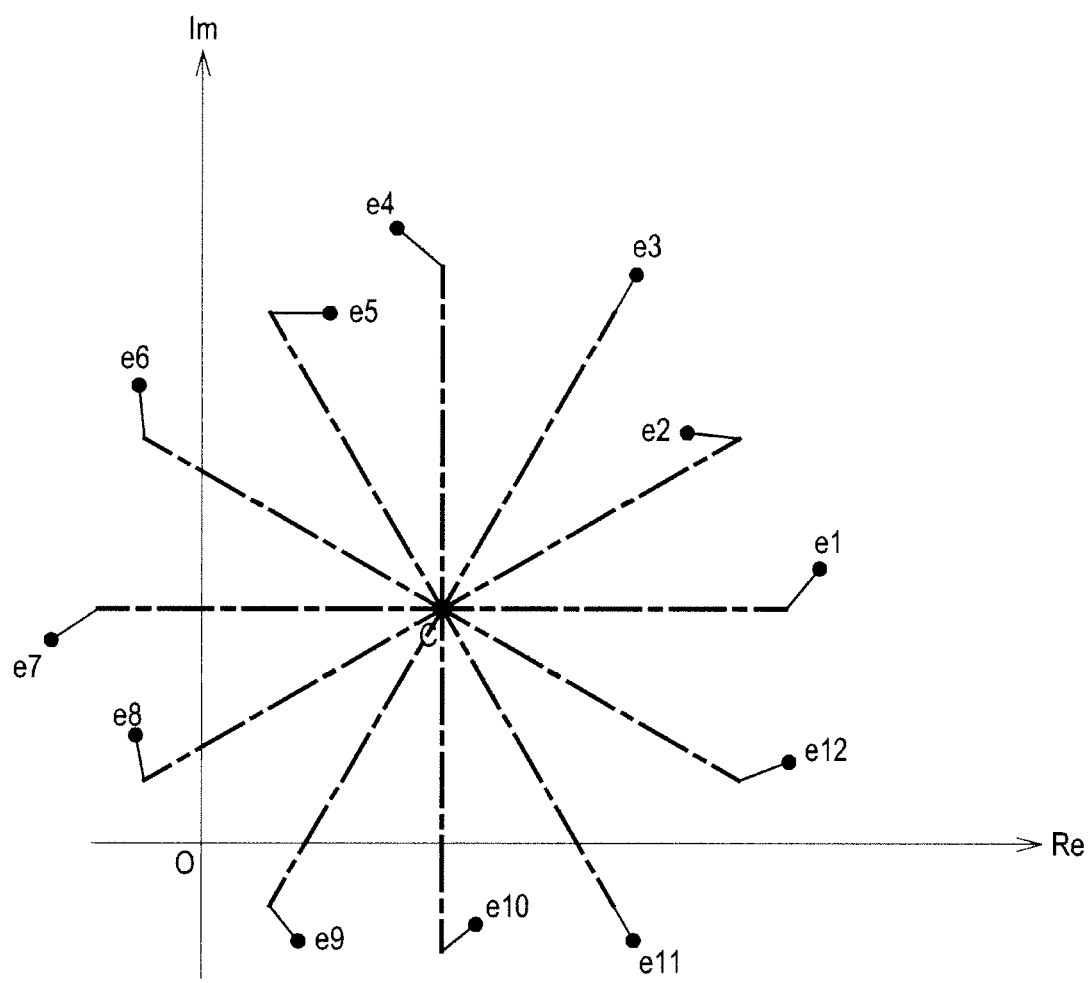
FIG. 9 is a schematic diagram showing an example of locating the plurality of ultrasound data corresponding to the tissues and the blood flow on the complex plane, wherein the tissues comprise the tissue that does not move within the target object and the tissue that moves at the constant speed.

FIG. 9 is a schematic diagram showing an example of locating the plurality of ultrasound data corresponding to the tissues and the blood flow on the complex plane, wherein the tissues comprise the tissue that does not move within the target object and the tissue that moves at the constant speed. The data processing section 131 may be configured to analyze the plurality of ultrasound data e1 to e12 acquired from the tissues and the blood flow. The data processing section 131 may further locate the plurality of ultrasound data e1 to e12, which overlap speed components (shown by dotted lines) corresponding to the tissue with speed components (shown by lines) corresponding to the blood flow, on the complex plane as shown in FIG. 9. The plurality of ultrasound data may be located on the complex plane with the speed component (i.e., DC component) of the tissue that does not move within the target object as the center point C apart from the origin O of the complex plane.

Figure 10:
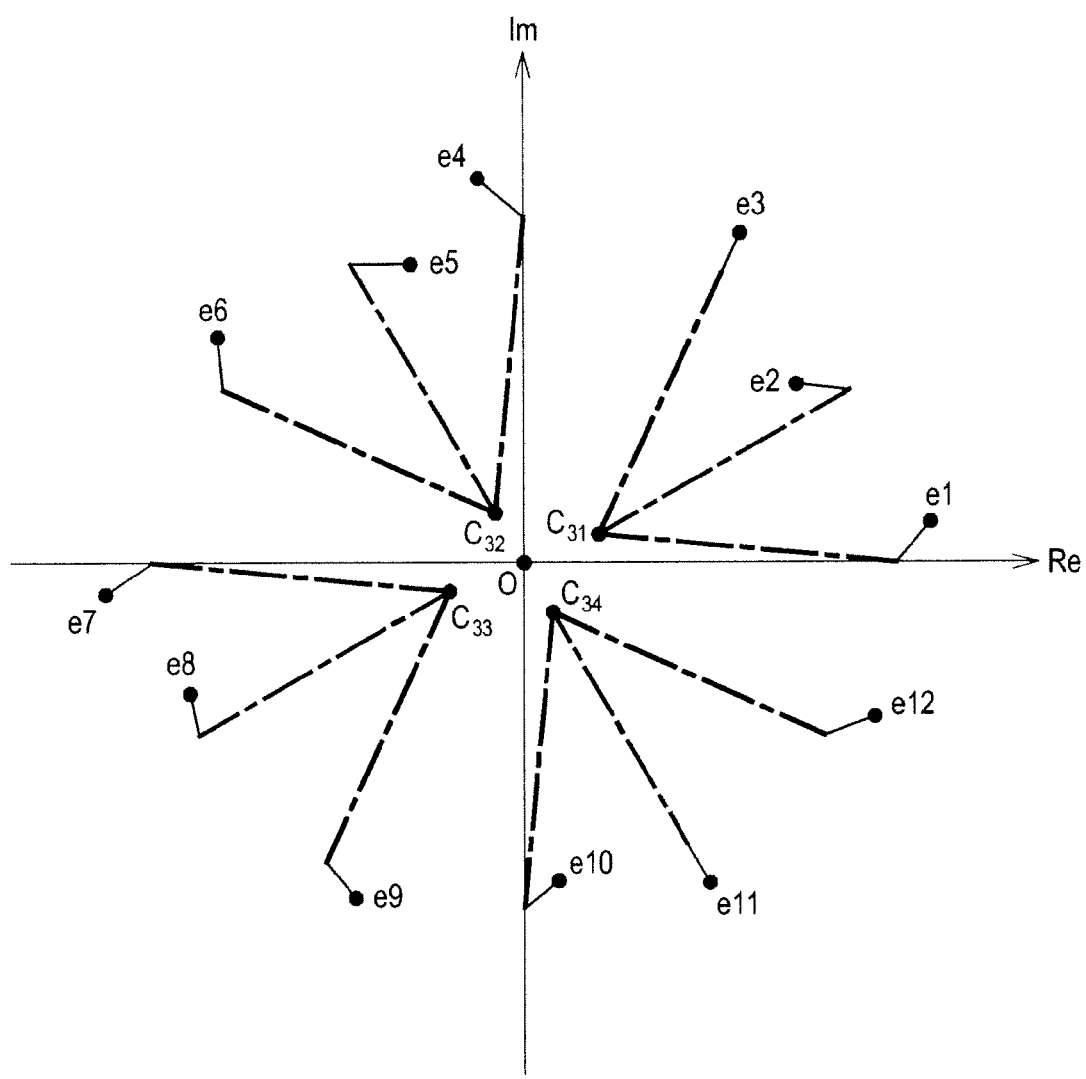
FIG. 10 is a schematic diagram showing an example of locating the plurality of ultrasound data corresponding to the tissue and the blood flow, wherein the tissue moves at a low speed within the target object.

FIG. 10 is a schematic diagram showing an example of locating the plurality of ultrasound data corresponding to the tissue and the blood flow, wherein the tissue moves at a low speed within the target object. The data processing section 131 may be configured to analyze the plurality of ultrasound data e1 to e12 acquired from the tissue and the blood flow. The data processing section 131 may further locate the plurality of ultrasound data e1 to e12, which overlap speed components (shown by dotted lines) corresponding to the tissue with speed components (shown by lines) corresponding to the blood flow, on the complex plane with the center points C31 to C34 as shown in FIG. 10.

Referring back to FIG. 4, the circle fitting section 132 may be configured to form a plurality of ultrasound data groups based on the plurality of ultrasound data located on the complex plane by the data processing section 131. Each of the plurality of ultrasound data groups may include a predetermined number of ultrasound data. The circle fitting section 132 may further perform a circle fitting upon each of the plurality of ultrasound data groups. The methods of performing the circle fitting are well known in the art. For example, the circle fitting may include RANSAC circle fitting, a least-square circle fitting, an S-parameter circle fitting and the like.

Examples of performing the circle fitting upon the plurality of ultrasound data located on the complex plane in consideration of the speeds of the tissue and the blood flow, which exist within the target object, will be described in view of FIGS. 11 to 13.

Figure 11:
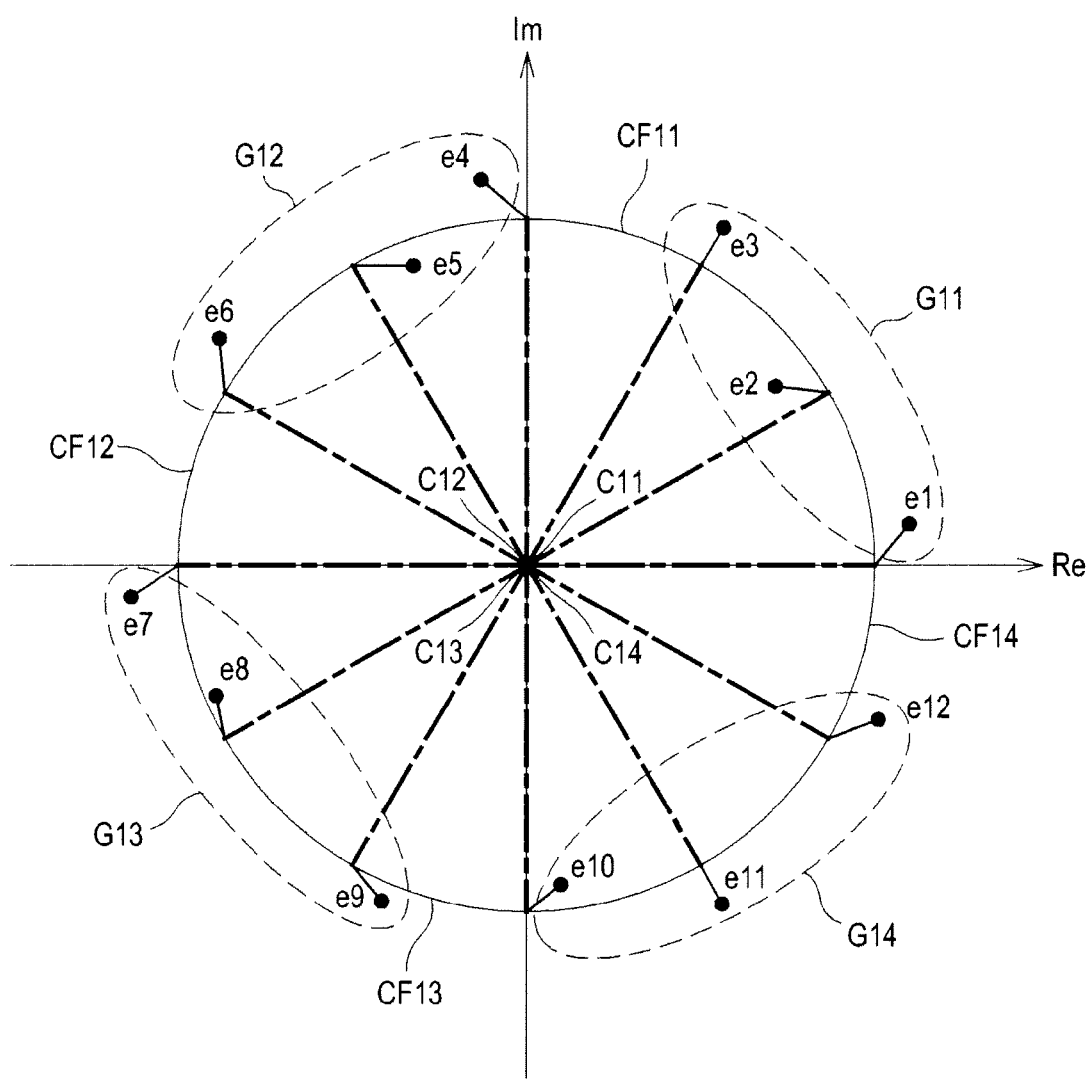
FIG. 11 is a schematic diagram showing an example of performing a circle fitting upon the plurality of ultrasound data corresponding to the tissue and the blood flow, wherein the tissue moves at the constant speed within the target object.

FIG. 11 is a schematic diagram showing an example of performing the circle fitting upon the plurality of ultrasound data corresponding to the tissue and the blood flow, wherein the tissue moves at the constant speed within the target object. The circle fitting section 132 may be configured to group the plurality of ultrasound data e1 to e12 located on the complex plane as shown in FIG. 8 into the plurality of ultrasound data groups G11 to G14 as shown in FIG. 11. Each of the plurality of ultrasound data groups G11 to G14 may include three ultrasound data. That is, a first ultrasound data group G11 may include ultrasound data e1 to e3, a second ultrasound data group G12 may include ultrasound data e4 to e6, a third ultrasound data group G13 may include ultrasound data e7 to e9 and a fourth ultrasound data group G14 may include ultrasound data e10 to e12. The circle fitting section 132 may further perform the circle fitting upon the ultrasound data corresponding to each of the plurality of ultrasound data groups G11 to G14 to thereby set circumferences CF11 to CF14 corresponding to each of the ultrasound data group as shown in FIG. 11.

Figure 12:
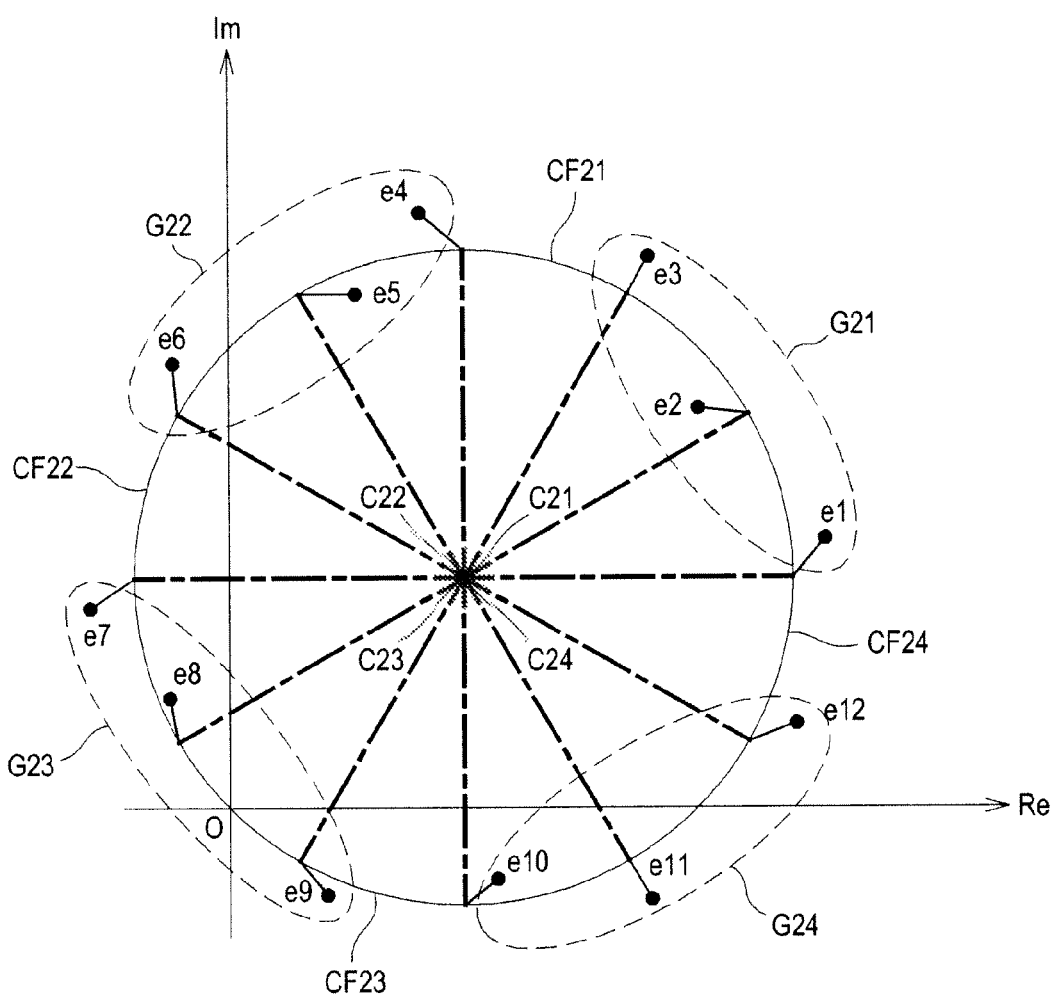
FIG. 12 is a schematic diagram showing an example of performing the circle fitting upon the plurality of ultrasound data corresponding to the tissues and the blood flow, wherein the tissues comprise the tissue that does not move within the target object and the tissue that moves at the constant speed within the target object.

FIG. 12 is a schematic diagram showing an example of performing the circle fitting upon the plurality of ultrasound data corresponding to the tissues and the blood flow, wherein the tissues comprise the tissue that does not move within the target object and the tissue that moves at the constant speed within the target object. The circle fitting section 132 may be configured to group the plurality of ultrasound data e1 to e12 located on the complex plane as shown in FIG. 9 into a plurality of ultrasound data groups G21 to G24 as shown in FIG. 12. Each of the ultrasound data groups G21 to G24 may include three ultrasound data. That is, a first ultrasound data group G21 may include the ultrasound data e1 to e3, a second ultrasound data group G22 may include the ultrasound data e4 to e6, a third ultrasound data group G23 may include the ultrasound data e7 to e9, and the fourth ultrasound data group G24 may include the ultrasound data e10 to e12. The circle fitting section 132 may further perform the circle fitting upon the ultrasound data corresponding to each of the ultrasound data groups G21 to G24 to thereby set circumferences CF21 to CF24 corresponding to each of the ultrasound data groups G21 to G24 as shown in FIG. 12.

Figure 13:
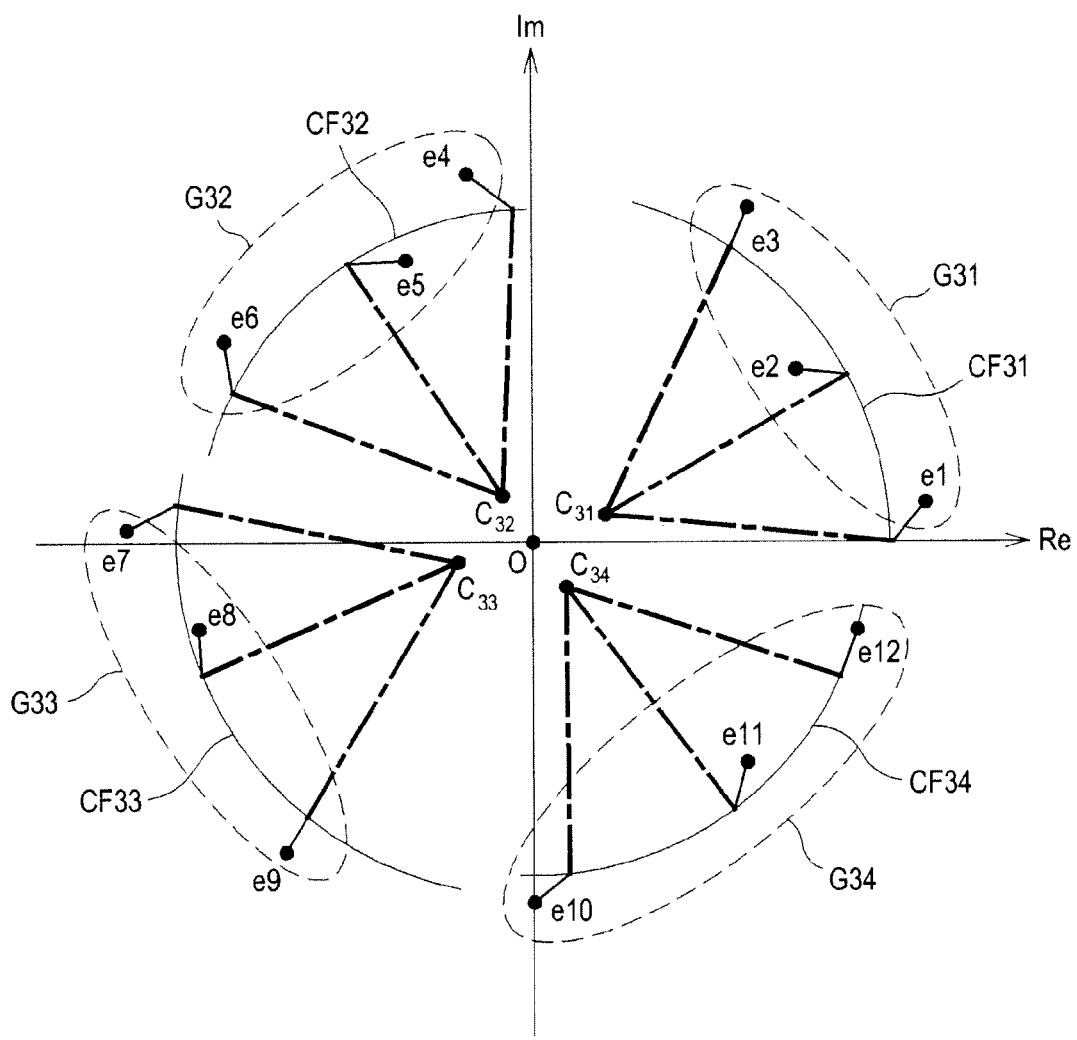
FIG. 13 is a schematic diagram showing an example of performing the circle fitting upon the plurality of ultrasound data corresponding to the tissue and the blood flow, wherein the tissue moves at the low speed within the target object.

FIG. 13 is a schematic diagram showing an example of performing the circle fitting upon the plurality of ultrasound data corresponding to the tissue and the blood flow, wherein the tissue moves at the low speed within the target object. The circle fitting section 132 may be configured to group the plurality of ultrasound data e1 to e12 located on the complex plane as shown in FIG. 10 into a plurality of ultrasound data groups G31 to G34 as shown in FIG. 13. Each of the ultrasound data groups G31 to G34 may include three ultrasound data. That is, a first ultrasound data may include the ultrasound data e1 to e3, a second ultrasound data may include the ultrasound data e4 to e6, a third ultrasound data may include the ultrasound data e7 to e9, and a fourth ultrasound data may include the ultrasound data e10 to e12. The circle fitting section 132 may further perform the circle fitting upon the ultrasound data corresponding to each of the ultrasound data groups G31 to G34 to thereby set circumferences CF31 to CF34 corresponding to each of the ultrasound data groups G31 to G34 as shown in FIG. 13.

Referring back to FIG. 4, the center point detecting section 133 may be configured to detect center points of the circumferences corresponding to the plurality of ultrasound data groups based on the circumferences set by the circle fitting section 132. As one example, the center point detecting section 133 may detect center points C11 to C14 of each of the circumferences CF11 to CF14 corresponding to the plurality of ultrasound data groups G11 to G14 as shown in FIG. 11. As another example, the center point detecting section 133 may detect center points C21 to C24 of each of the circumferences CF21 to CF24 corresponding to the plurality of ultrasound data groups G21 to G24 as shown in FIG. 12. As yet another example, the center point detecting section 133 may detect center points C31 to C34 of each of the circumferences CF31 to CF34 corresponding to the plurality of ultrasound data groups G31 to G34 as shown in FIG. 13. The methods of detecting the center points are well known in the art. Thus, they have not been described in detail so as not to unnecessarily obscure the present disclosure.

The determining section 134 may be configured to analyze the plurality of center points detected by the center point detecting section 133. The determining section 134 may further determine whether the plurality of the center points are located on the same position and whether located on the origin of the complex plane to thereby form determination information.

As one example, the determining section 134 may be configured to analyze the center points C11 to C14 corresponding to the plurality of circumferences CF11 to CF14 as shown in FIG. 11. The determining section 134 may further determine whether the plurality of center points C11 to C14 are located on the same position and whether located on the origin of the complex plane. If it is determined that the plurality of center points C11 to C14 are located on the same position and located on the origin of the complex plane, then the determining section 134 may form first determination information. The first determination information may be the information representing that the plurality of center points C11 to C14 are located on the same position and located on the origin of the complex plane. That is, the first determination information may be information representing that the tissue and the blood flow exist within the target object, wherein the tissue moves at the constant speed.

As another example, the determining section 134 may be configured to analyze the center points C21 to C24 corresponding to the plurality of circumferences CF21 to CF24 as shown in FIG. 12. The determining section 134 may further determine whether the plurality of center points C21 to C24 are located on the same position and whether located on the origin of the complex plane. If it is determined that the plurality of center points C21 to C24 are located on the same position but not located on the origin of the complex plane, then the determining section 134 may form second determination information. The second determination information may be the information representing that the plurality of center points C21 to C24 are located on the same position but not located on the origin of the complex plane. That is, the second determination information may be the information representing that the tissues and the blood flow exist within the target object, wherein the tissues comprise the tissue that does not move and the tissue that moves at the constant speed.

As yet another example, the determining section 134 may be configured to analyze the center points C31 to C34 corresponding to the plurality of the circumferences CF31 to CF34 shown in FIG. 13. The determining section 134 may further determine whether the plurality of center points C31 to C34 are located on the same position and whether located on the origin of the complex plane. If it is determined that the plurality of center points C31 to C34 are neither located on the same position nor on the origin of the complex plane, then the determining section 134 may form third determination information. The third determination information may be the information representing that the plurality of center points C31 to C34 are neither located on the same position nor on the origin of the complex plane. That is, the third determination information may be the information representing that the tissue and the blood flow exist within the target object, wherein the tissue moves at the low speed.

The filtering section 135 may be configured to perform a downmixing and a clutter filtering upon the plurality of ultrasound data based on the determination information provided from the determining section 134.

Examples of performing the downmixing and the clutter filtering upon the plurality of ultrasound data will be described with reference to FIGS. 14 to 16.

Figure 14:
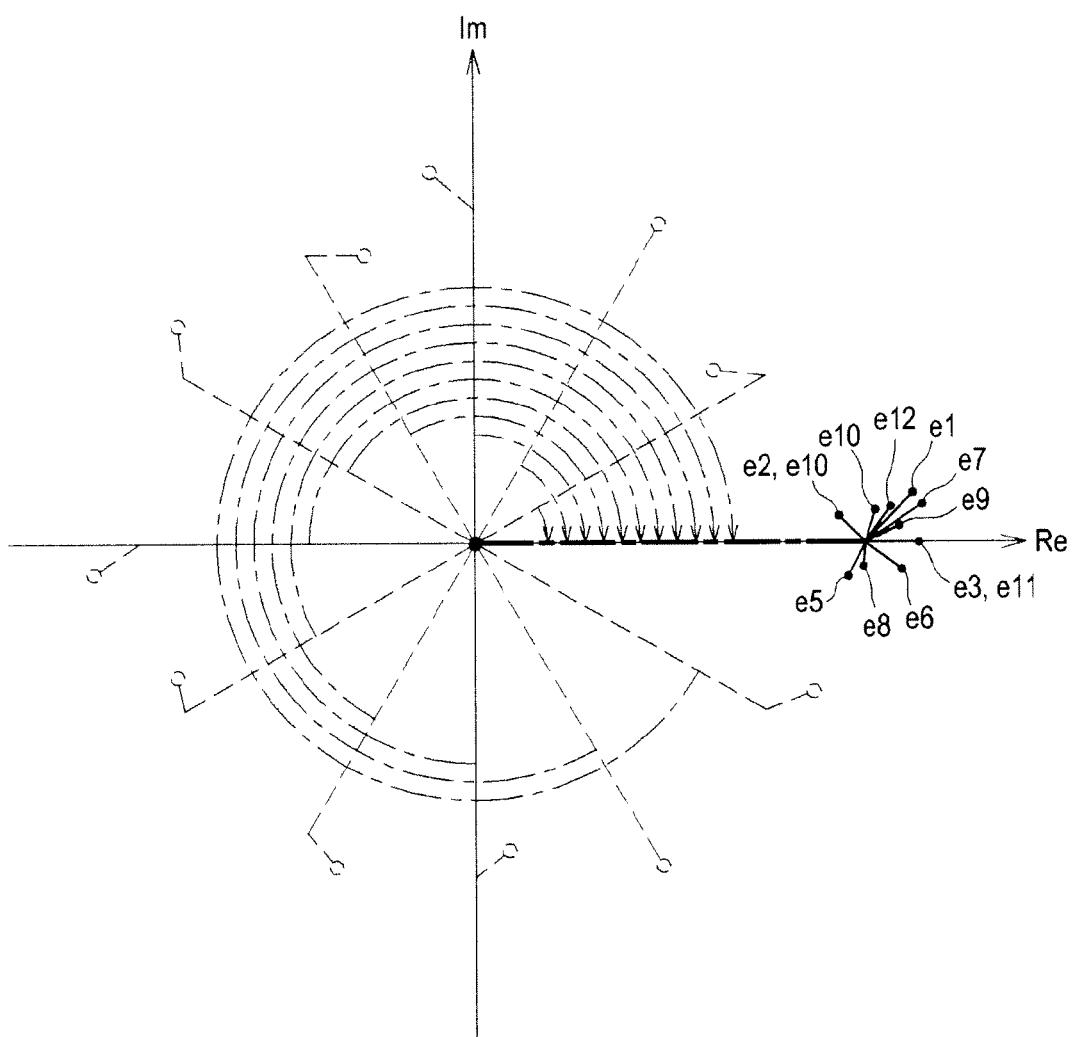
FIG. 14 is a schematic diagram showing an example of performing a downmixing upon the plurality of ultrasound data corresponding to the tissue and the blood flow, wherein the tissue moves at the constant speed.

FIG. 14 is a schematic diagram showing an example of performing the downmixing upon the plurality of ultrasound data corresponding to the tissue and the blood flow, wherein the tissue moves at the constant speed. The filtering section 135 may be configured to perform the downmixing, which rotates each of the plurality of ultrasound data e1 to e12 into a real axis of the complex plane with the center point at the origin O of the complex plane based on the first determination information provided from the determining section 134, upon the plurality of ultrasound data e1 to e12 as shown in FIG. 14. More particularly, the filtering section 135 may perform the downmixing, which performs a phase shift (0°) upon the ultrasound data e1 based on the first determination information. The filtering section 135 may further perform the downmixing, which performs a phase shift (−θ) upon the ultrasound data e2 based on the first determination information. The filtering section 135 may further perform the downmixing, which performs a phase shift (−2θ) upon the ultrasound data e3 based on the first determination information. The filtering section 135 may further perform the downmixing on the ultrasound data e4 to e12 as described above. As to performing the downmixing upon each of the plurality of ultrasound data, the speed components corresponding to clutter signals moves to DC component. The filtering section 135 may further perform the clutter filtering upon the downmixed ultrasound data to thereby filter the speed components (i.e., DC component) corresponding to the clutter signals from the downmixed ultrasound data.

Figure 15:
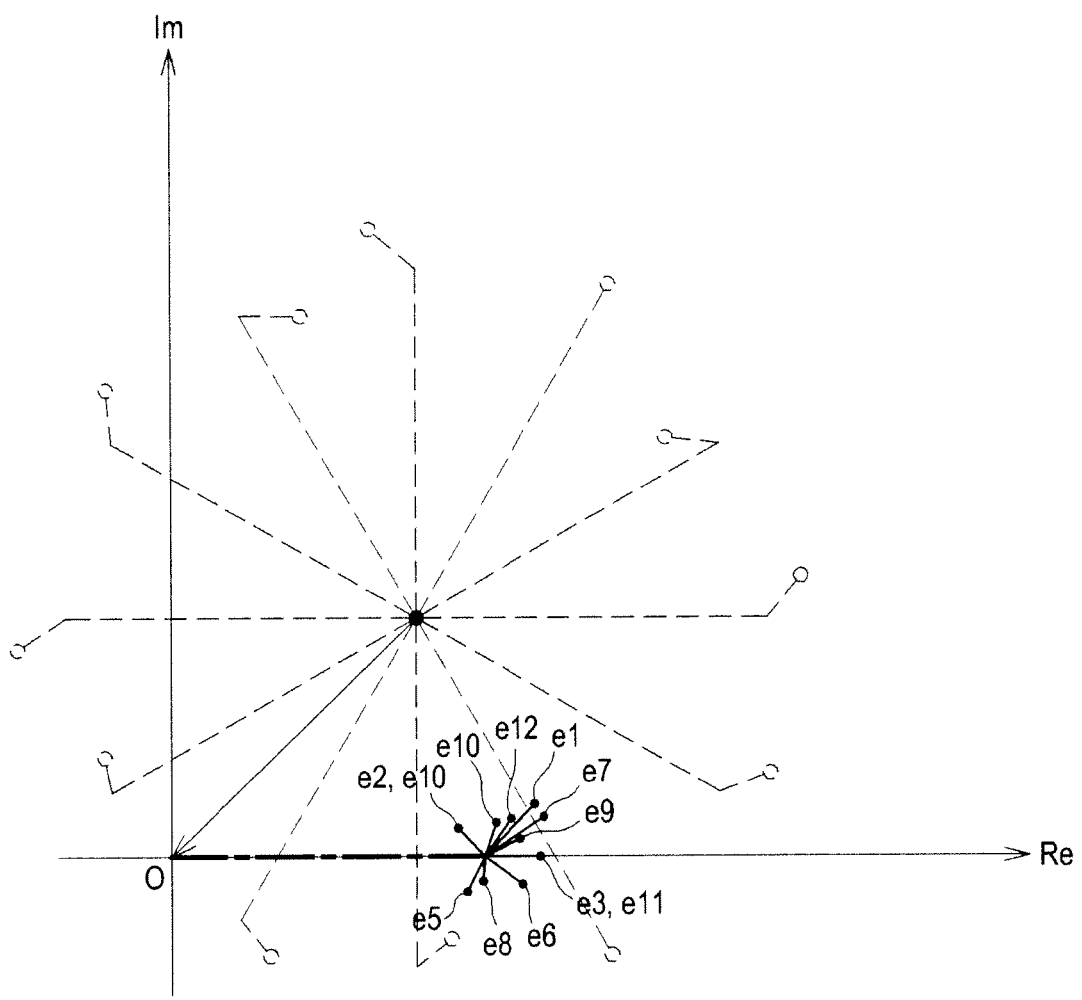
FIG. 15 is a schematic diagram showing an example of performing the downmixing upon the plurality of ultrasound data corresponding to the tissues and the blood flow, wherein the tissues comprise the tissue that does not move within the target object and the tissue that moves at the constant speed within the target object.

FIG. 15 is a schematic diagram showing an example of performing the downmixing upon the plurality of ultrasound data corresponding to the tissues and the blood flow, wherein the tissues comprise the tissue that does not move within the target object and the tissue that moves at the constant speed within the target object. The filtering section 135 may be configured to perform the downmixing upon each of the plurality of ultrasound data e1 to e12 based on the second determination information provided from the determining section 134 as shown in FIG. 15. More particularly, the filtering section 135 may move the center points of the circumferences corresponding to the ultrasound data e1 to e12 to the origin O of the complex plane based on the second determination information. The filtering section 135 may further perform the downmixing, which rotates each of the plurality of ultrasound data e1 to e12 into the real axis based on the origin O of the complex plane as described above. That is, the filtering section 135 may perform the downmixing, which performs a phase shift (0°) on the ultrasound data e1 based on the second determination information. The filtering section 135 may further perform the downmixing, which performs a phase shift (−θ) on the ultrasound data e2 based on the second determination information. The filtering section 135 may further perform the downmixing, which performs a phase shift (−2θ) on the ultrasound data e3 based on the second determination information. The filtering section 135 may further perform the downmixing on the ultrasound data e4 to e12 as described above. As to performing the downmixing upon each of the plurality of ultrasound data, the speed components corresponding to clutter signals move to DC component. The filtering section 135 may further perform the clutter filtering upon the downmixed ultrasound data to thereby filter the speed components (i.e., DC component) corresponding to the clutter signals from the plurality of the ultrasound data.

It was explained in the above embodiment that the filtering section 135 may move the center points of the circumferences corresponding to the plurality of ultrasound data to the origin of the complex plane, and perform the downmixing on each of the ultrasound data. However, the filtering section 135 may further set any ultrasound data (e.g., first ultrasound data e1) among the plurality of ultrasound data e1 to e12 as a reference ultrasound data, perform the downmixing, which rotates each of the ultrasound data into the reference ultrasound data, upon the plurality of ultrasound data, and move the center points of the circumferences to the origin of the complex plane.

Figure 16:
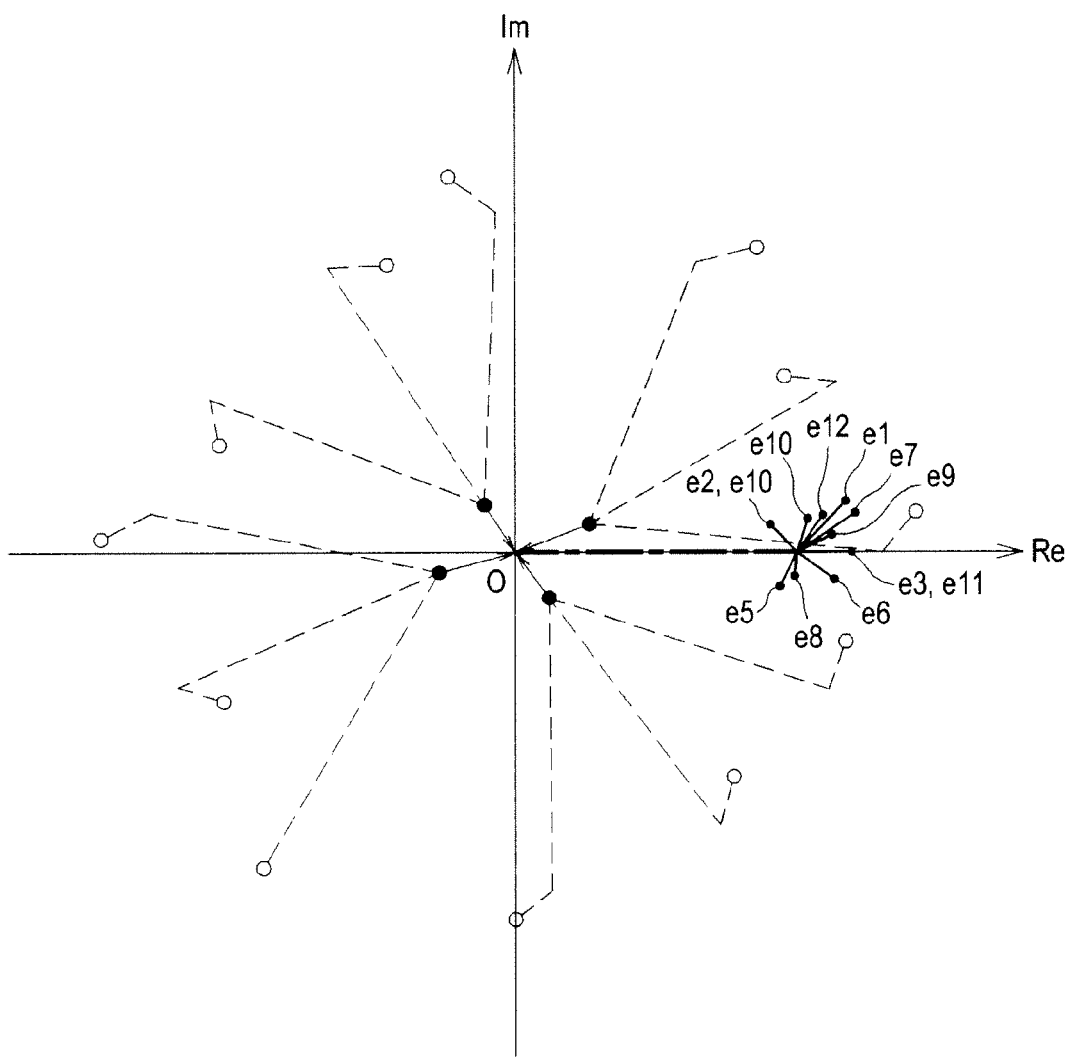
FIG. 16 is a schematic diagram showing an example of performing the downmixing upon the plurality of ultrasound data corresponding to the tissue and the blood flow, wherein the tissue moves at the low speed within the target object.

FIG. 16 is a schematic diagram showing an example of performing the downmixing upon the plurality of ultrasound data corresponding to the tissue and the blood flow, wherein the tissue moves at the low speed within the target object. The filtering section 135 may be configured to perform the downmixing upon each of the ultrasound data e1 to e12 based on the third determination information provided from the determining section 134 as shown in FIG. 16. More particularly, the filtering section 135 may move the center points of the plurality of circumferences corresponding to the plurality of ultrasound data e1 to e12 to the origin O of the complex plane based on the third determination information. The filtering section 135 may further perform the downmixing that rotates each of the ultrasound data e1 to e12 into the real axis of the complex plane based on the origin O of the complex plane as described above. As to performing the downmixing on each of the ultrasound data, the speed components corresponding to clutter signals move to the DC component. The filtering section 135 may further perform the clutter filtering on the plurality of ultrasound data to thereby filter the speed components (i.e., DC component) corresponding to the clutter signals from the plurality of the ultrasound data.

Referring back to FIG. 4, the image forming section 136 may be configured to form a Doppler mode image based on the plurality of ultrasound image downmixed and clutter-filtered by the filtering section 135.

Referring back to FIG. 1, the storage unit 140 may store the plurality of ultrasound data acquired from the ultrasound data acquisition unit 110. The storage unit 140 may further store the plurality of ultrasound data filtered by the processing unit 130. The display unit 150 may display the Doppler mode image formed by the processing unit 130.

In another embodiment, there is provided a method of performing a clutter filtering, comprising: a) acquiring a plurality of ultrasound data corresponding to a target object including at least one of a tissue and a blood flow, wherein the plurality of ultrasound data are ultrasound data for obtaining a color Doppler mode image; b) locating each of the plurality of ultrasound data on a complex plane; c) performing a circle fitting on the plurality of ultrasound data located on the complex plane; and d) performing a downmixing and a clutter filtering on the circle-fitted ultrasound data in consideration of speed of the tissue.

In yet another embodiment, the present invention may provide a computer readable medium comprising computer executable instructions configured to perform the following acts: a) acquiring a plurality of ultrasound data corresponding to a target object including at least one of a tissue and a blood flow, wherein the plurality of ultrasound data are ultrasound data for obtaining a color Doppler mode image; b) locating each of the plurality of ultrasound data on a complex plane; c) performing a circle fitting on the plurality of ultrasound data located on the complex plane; and d) performing a downmixing and a clutter filtering on the circle-fitted ultrasound data in consideration of speed of the tissue. The computer readable medium may comprise a floppy disk, a hard disk, a memory, a compact disk, a digital video disk, etc.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

As an example, while only the processing unit 130 may perform the circle fitting, the downmixing and the clutter filtering upon the plurality of ultrasound data acquired from the ultrasound data acquisition unit 120, the processing unit 130 may further perform the circle fitting, the downmixing and the clutter filtering on a plurality of ultrasound data provided from external devices (e.g., a personal computer, a storage medium, etc.) which connect to the ultrasound system.

What is claimed is:

1. An ultrasound system, comprising:
   an ultrasound data acquisition device configured to transmit and receive ultrasound signals to and from a target object to thereby output a plurality of ultrasound data for obtaining a color Doppler mode image, wherein the target object includes at least one of a tissue and a blood flow; and
   a processor placed in communication with the ultrasound data acquisition device and being configured to locate the plurality of ultrasound data on a complex plane, the processor being further configured to perform a circle fitting upon the plurality of ultrasound data located on the complex plane to thereby set circumferences corresponding to the plurality of ultrasound data, detect center points of the circumferences, analyze the detected center points and determine whether the detected center points are located on a same position as an origin of the complex plane to thereby form determination information and perform a downmixing and a clutter filtering upon the circle-fitted ultrasound data in consideration of speed of the tissue based on the determination information,
   wherein the ultrasound data comprise in-phase/quadrature data.

2. The ultrasound system of claim 1, wherein the processor is configured to:
   group the plurality of ultrasound data located on the complex plane into a plurality of ultrasound data group, wherein each of the plurality of ultrasound data group comprises a predetermined number of ultrasound data; and
   perform the circle fitting upon each of the plurality of ultrasound data group to thereby set the circumferences corresponding to the plurality of ultrasound data group.

3. The ultrasound system of claim 2, wherein the processor is configured to detect the center points of the circumferences corresponding to the plurality of ultrasound data group.

4. The ultrasound system of claim 1, wherein the determination information comprises:
   first determination information representing that the detected center points are located on the same position as the origin of the complex plane;
   second determination information representing that the detected center points are located on the same position, but not located on the origin of the complex plane; and
   third determination information representing that the detected center points are neither located on the same position nor on the origin of the complex plane.

5. The ultrasound system of claim 4, wherein the processor is configured to:
   perform the downmixing for rotating each of the plurality of ultrasound data into a real axis of the complex plane with the center point at the origin of the complex plane based on the first determination information; and
   perform the clutter filtering upon the downmixed ultrasound data.

6. The ultrasound system of claim 4, wherein the processor is configured to:
   move the center points of the circumferences corresponding to the plurality of ultrasound data to the origin of the complex plane based on the second determination information;
   perform the downmixing for rotating each of the plurality of ultrasound data into a real axis of the complex plane based on the origin of the complex plane; and
   perform the clutter filtering on the downmixed ultrasound data.

7. The ultrasound system of claim 4, wherein the processor is configured to:
   set any ultrasound data among the plurality of ultrasound data as a reference ultrasound data based on the second determination information;
   perform the downmixing for rotating each of the plurality of ultrasound data into the reference ultrasound data based on the center points of the circumferences; and
   move the center points of the circumferences corresponding to the plurality of ultrasound data to the origin of the complex plane.

8. The ultrasound system of claim 4, wherein the processor is configured to:
   move the center points of the circumferences corresponding to the plurality of ultrasound data into the origin of the complex plane based on the third determination information;
   perform the downmixing for rotating each of the plurality of ultrasound data into a real axis of the complex plane based on the origin of the complex plane; and
   perform the clutter filtering upon the downmixed ultrasound data.

9. A method of performing a clutter filtering, comprising:
   a) acquiring a plurality of ultrasound data corresponding to a target object including at least one of a tissue and a blood flow, wherein the plurality of ultrasound data are ultrasound data for obtaining a color Doppler mode image;
   b) locating each of the plurality of ultrasound data on a complex plane;
   c) performing a circle fitting on the plurality of ultrasound data located on the complex plane to thereby set circumferences corresponding to the plurality of ultrasound data:
   d) detecting center points of the circumferences;
   e) analyzing the detected center points and determine whether the detected center points are located on a same position as an origin of the complex plane to thereby form determination information; and
   f) performing a downmixing and a clutter filtering on the circle-fitted ultrasound data in consideration of speed of the tissue based on the determination information, wherein the ultrasound data comprise in-phase/quadrature data.

10. The method of claim 9, the step c) comprises:
grouping the plurality of ultrasound data located on the complex plane into a plurality ultrasound data group, wherein each of the plurality of ultrasound data group comprises a predetermined number of ultrasound data; and
performing the circle fitting upon each of the plurality of ultrasound data group to thereby set the circumferences corresponding to the plurality of ultrasound data group.

11. The method of claim 9, wherein the determination information comprises:
first determination information representing that the detected center points are located on the same position as the origin of the complex plane;
second determination information representing that the detected center points are located on the same position but not located on the origin of the complex plane; and
third determination information representing that the detected center points are neither located on the same position nor on the origin of the complex plane.

12. The method of claim 11, wherein the step f) comprises:
performing the downmixing for rotating each of the plurality of ultrasound data into a real axis of the complex plane with the center point at the origin of the complex plane based on the first determination information; and
performing the clutter filtering upon the downmixed ultrasound data.

13. The method of claim 11, wherein the step f) comprises:
moving the center points of the circumferences corresponding to the plurality of ultrasound data to the origin of the complex plane based on the second determination information;
performing the downmixing for rotating each of the plurality of ultrasound data into a real axis of the complex plane based on the origin of the complex plane; and
performing the clutter filtering upon the downmixed ultrasound data.

14. The method of claim 11, wherein the step f) comprises:
setting any ultrasound data among the plurality of ultrasound data as a reference ultrasound data based on the second determination information;
performing the downmixing for rotating each of the plurality of ultrasound data into the reference ultrasound data based on the center points of the circumferences; and
moving the center points of the circumferences corresponding to the plurality of ultrasound data to the origin of the complex plane.

15. The method of claim 11, wherein the step f) comprises:
moving the center points of the circumferences corresponding to the plurality of ultrasound data to the origin of the complex plane based on the third determination information:
performing the downmixing for rotating each of the plurality of ultrasound data into a real axis of the complex plane based on the origin of the complex plane; and
performing the clutter filtering on the downmixed ultrasound data.

16. A non-transitory computer readable medium comprising computer executable instructions configured to perform following acts:
a) acquiring a plurality of ultrasound data corresponding to a target object including at least one of a tissue and a blood flow, wherein the plurality of ultrasound data are ultrasound data for obtaining a color Doppler mode image;
b) locating each of the plurality of ultrasound data on a complex plane;
c) performing a circle fitting on the plurality of ultrasound data located on the complex plane to thereby set circumferences corresponding to the plurality of ultrasound data;
d) detecting center points of the circumferences;
e) analyzing the detected center points and determine whether the detected center points are located on a same position and located on an origin of the complex plane to thereby form determination information; and
f) performing a downmixing and a clutter filtering on the circle-fitted ultrasound data in consideration of speed of the tissue based on the determination information,
wherein the ultrasound data comprise in-phase/quadrature data.

* * * * *